United States Patent [19]
Zentgraf et al.

[11] Patent Number: 6,051,384
[45] Date of Patent: Apr. 18, 2000

[54] METHOD OF DETECTING P53-SPECIFIC ANTIBODIES

[75] Inventors: Hanswalter Zentgraf, Heidelberg; Peter Schranz, Durmersheim; Martin Volkmann, Heidelberg; Claudia Tessmer, Schwarzach; Ralf Klein, Karlsruher, all of Germany

[73] Assignee: Deutsches Krebsforschungszentrum Stiftung des Offentlichen Rechts, Heidelberg, Germany

[21] Appl. No.: 08/244,476

[22] PCT Filed: Sep. 30, 1993

[86] PCT No.: PCT/EP93/02666

§ 371 Date: Sep. 15, 1994

§ 102(e) Date: Sep. 15, 1994

[87] PCT Pub. No.: WO94/08241

PCT Pub. Date: Apr. 14, 1994

[30] Foreign Application Priority Data

Sep. 30, 1992 [DE] Germany ............... 42 32 823

[51] Int. Cl.[7] ............ G01N 33/53; G01N 33/574; A61K 38/00; C07H 21/04
[52] U.S. Cl. ............ 435/7.1; 435/7.23; 435/810; 435/975; 530/324; 530/325; 530/326; 536/23.5; 536/23.1
[58] Field of Search ............ 435/7.23, 7.1, 435/91.1, 91.4, 810, 975; 436/506, 523, 63, 64, 800; 536/23.1, 23.5; 530/324, 325, 326

[56] References Cited

U.S. PATENT DOCUMENTS 5,652,115  7/1997  Marks et al. .............. 435/7.23

FOREIGN PATENT DOCUMENTS 2253211  9/1992  United Kingdom .

WO 92/13970  8/1992  WIPO .

OTHER PUBLICATIONS

Harlow et al, "Antibodies: A laboratory Manual" Cold Spring Harbor Laboratory, Chapter 14, pp.555–566 and 590, 1988.

Harris et al, "Molecular basis for heterogeneity of the human p53 protein" Mol. Cell. Biol., vol. 6, No. 12, p. 4650–4656, Dec. 1986.

Lamb et al, "Characterization of the human p53 gene", Mol. Cell Biology, vol. 6, No. 5, p. 1379–1385, May 1986.

Vojtesek et al, "An immunochemical analysis of the human nuclear phosphorprotein p53", J. of Immunol. Methods, vol. 151, p. 237–244, Jun. 1992.

Hassapoglidou et al, Antibodies to the p53 Tumor Suppressor Gene Product Quantified in Cancer Patient Serum With a Time–Resolved Immunofluormetric Technique, Dec. 1992.

*Primary Examiner*—Yvonne Eyler
*Attorney, Agent, or Firm*—Venable

[57] ABSTRACT

The invention relates to a method of detecting p53-specific antibodies in body fluids wherein support-bound p53 and/or support-bound fragments thereof comprising binding regions for p53-specific antibodies are incubated with body fluids and the specific antibodies (a) bound to p53 and/or said fragments are allowed to react

- with labelled antibodies (b) directed against antibodies (a), or
- with unlabelled antibodies (b) while the latter are allowed to react with labelled antibodies (c) directed against antibodies (b), with the labelling being non-radioactive in either case.

The invention further relates to a kit useful therefor. Also, the invention relates to p53 fragments and DNA sequences coding for them, said fragments comprising binding regions for p53-specific antibodies, as well as to methods of preparing them.

9 Claims, No Drawings

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "Synthetic primer"

(iii) HYPOTHETICAL: NO (xi) SEQUENCE DESCRIPTION: SEQ ID NO:1:

GCATGGATCC GAATTCTGCC TTCCGGGTCA CTGC         34

(2) INFORMATION FOR SEQ ID NO:2:

(i) SEQUENCE CHARACTERISTICS:

(A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iii) HYPOTHETICAL: NO (xi) SEQUENCE DESCRIPTION: SEQ ID NO:2:

GGTACCCGGG GATCCTGGGT GCTTCTGACG                                          30

(2) INFORMATION FOR SEQ ID NO:3:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iii) HYPOTHETICAL: NO (xi) SEQUENCE DESCRIPTION: SEQ ID NO:3:

CGCGGATCCA TGGAGGAGCC GCAGTCAG                                            28

(2) INFORMATION FOR SEQ ID NO:4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iii) HYPOTHETICAL: NO (xi) SEQUENCE DESCRIPTION: SEQ ID NO:4:

CGCGGATCCT CAATGGTGAT GGTGATGGTG GTCTGAGTCA GGCCCTTCTG                    50

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iii) HYPOTHETICAL: NO (xi) SEQUENCE DESCRIPTION: SEQ ID NO:5:

CGCGGATCCA TGGAGGAGCC GCAGTCAG                                            28

(2) INFORMATION FOR SEQ ID NO:6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iii) HYPOTHETICAL: NO (xi) SEQUENCE DESCRIPTION: SEQ ID NO:6:

CGCGGATCCT CAAGTGAACC ATTGTTCAAT ATCGTCCG                        38

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iii) HYPOTHETICAL: NO (xi) SEQUENCE DESCRIPTION: SEQ ID NO:7:

CGCGGATCCA ACGTTCTGTC CCCCTTGCCG                                 30

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iii) HYPOTHETICAL: NO (xi) SEQUENCE DESCRIPTION: SEQ ID NO:8:

CGCGGATCCT CAAGCAGCCT CTGGCATTCT GGG                             33

(2) INFORMATION FOR SEQ ID NO:9:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iii) HYPOTHETICAL: NO (xi) SEQUENCE DESCRIPTION: SEQ ID NO:9:

CGCGGATCCT CAATGGTGAT GGTGATGGTG AGTGAACCAT TGTTCAATAT CGTCCG    56

(2) INFORMATION FOR SEQ ID NO:10:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthetic primer"

(iii) HYPOTHETICAL: NO (xi) SEQUENCE DESCRIPTION: SEQ ID NO:10:

CGCGGATCCT CAATGGTGAT GGTGATGGTG AGCAGCCTCT GGCATTCTGG G         51

(2) INFORMATION FOR SEQ ID NO:11:

(i) SEQUENCE CHARACTERISTICS:
        (A) LENGTH: 241 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:11:

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser
```

(2) INFORMATION FOR SEQ ID NO:12:

(i) SEQUENCE CHARACTERISTICS:
        (A) LENGTH: 310 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
Met Asp Asp Leu Met Leu Ser Pro Asp Asp Ile Glu Gln Trp Phe Thr
1               5                   10                  15

Glu Asp Pro Gly Pro Asp Glu Ala Pro Arg Met Pro Glu Ala Ala Pro
            20                  25                  30
```

```
Pro Val Ala Pro Ala Pro Ala Ala Pro Thr Pro Ala Ala Pro Ala Pro
            35                  40                  45

Ala Pro Ser Trp Pro Leu Ser Ser Val Pro Ser Gln Lys Thr Tyr
 50                      55                  60

Gln Gly Ser Tyr Gly Phe Arg Leu Gly Phe Leu His Ser Gly Thr Ala
 65                  70                  75                  80

Lys Ser Val Thr Cys Thr Tyr Ser Pro Ala Leu Asn Lys Met Phe Cys
                 85                  90                  95

Gln Leu Ala Lys Thr Cys Pro Val Gln Leu Trp Val Asp Ser Thr Pro
             100                 105                 110

Pro Pro Gly Thr Arg Val Arg Ala Met Ala Ile Tyr Lys Gln Ser Gln
             115                 120                 125

His Met Thr Glu Val Val Arg Arg Cys Pro His His Glu Arg Cys Ser
         130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                 165                 170                 175

Val Val Val Pro Tyr Glu Pro Pro Glu Val Gly Ser Asp Cys Thr Thr
             180                 185                 190

Ile His Tyr Asn Tyr Met Cys Asn Ser Ser Cys Met Gly Gly Met Asn
         195                 200                 205

Arg Arg Pro Ile Leu Thr Ile Ile Thr Leu Glu Asp Ser Ser Gly Asn
210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                 245                 250                 255

His His Glu Leu Pro Pro Gly Ser Thr Lys Arg Ala Leu Pro Asn Asn
             260                 265                 270

Thr Ser Ser Ser Pro Gln Pro Lys Lys Lys Pro Leu Asp Gly Glu Tyr
             275                 280                 285

Phe Thr Leu Gln Ile Arg Gly Arg Glu Arg Phe Glu Met Phe Arg Glu
 290                 295                 300

Leu Asn Glu Ala Leu Glu
305             310

(2) INFORMATION FOR SEQ ID NO:13:

(i) SEQUENCE CHARACTERISTICS:
        (A) LENGTH: 354 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:13:

Met Asp Asp Leu Met Leu Ser Pro Asp Asp Ile Glu Gln Trp Phe Thr
 1               5                  10                  15

Glu Asp Pro Gly Pro Asp Glu Ala Pro Arg Met Pro Glu Ala Ala Pro
             20                  25                  30

Pro Val Ala Pro Ala Pro Ala Ala Pro Thr Pro Ala Ala Pro Ala Pro
             35                  40                  45

Ala Pro Ser Trp Pro Leu Ser Ser Val Pro Ser Gln Lys Thr Tyr
 50                      55                  60
```

```
Gln Gly Ser Tyr Gly Phe Arg Leu Gly Phe Leu His Ser Gly Thr Ala
 65                  70                  75                  80

Lys Ser Val Thr Cys Thr Tyr Ser Pro Ala Leu Asn Lys Met Phe Cys
                 85                  90                  95

Gln Leu Ala Lys Thr Cys Pro Val Gln Leu Trp Val Asp Ser Thr Pro
            100                 105                 110

Pro Pro Gly Thr Arg Val Arg Ala Met Ala Ile Tyr Lys Gln Ser Gln
        115                 120                 125

His Met Thr Glu Val Val Arg Arg Cys Pro His His Glu Arg Cys Ser
    130                 135                 140

Asp Ser Asp Gly Leu Ala Pro Pro Gln His Leu Ile Arg Val Glu Gly
145                 150                 155                 160

Asn Leu Arg Val Glu Tyr Leu Asp Asp Arg Asn Thr Phe Arg His Ser
                165                 170                 175

Val Val Val Pro Tyr Glu Pro Pro Glu Val Gly Ser Asp Cys Thr Thr
            180                 185                 190

Ile His Tyr Asn Tyr Met Cys Asn Ser Ser Cys Met Gly Gly Met Asn
        195                 200                 205

Arg Arg Pro Ile Leu Thr Ile Ile Thr Leu Glu Asp Ser Ser Gly Asn
210                 215                 220

Leu Leu Gly Arg Asn Ser Phe Glu Val Arg Val Cys Ala Cys Pro Gly
225                 230                 235                 240

Arg Asp Arg Arg Thr Glu Glu Glu Asn Leu Arg Lys Lys Gly Glu Pro
                245                 250                 255

His His Glu Leu Pro Pro Gly Ser Thr Lys Arg Ala Leu Pro Asn Asn
            260                 265                 270

Thr Ser Ser Ser Pro Gln Pro Lys Lys Pro Leu Asp Gly Glu Tyr
        275                 280                 285

Phe Thr Leu Gln Ile Arg Gly Arg Glu Arg Phe Glu Met Phe Arg Glu
    290                 295                 300

Leu Asn Glu Ala Leu Glu Leu Lys Asp Ala Gln Ala Gly Lys Glu Pro
305                 310                 315                 320

Gly Gly Ser Arg Ala His Ser Ser His Leu Lys Ser Lys Lys Gly Gln
                325                 330                 335

Ser Thr Ser Arg His Lys Lys Leu Met Phe Lys Thr Glu Gly Pro Asp
            340                 345                 350

Ser Asp (2) INFORMATION FOR SEQ ID NO:14:

(i) SEQUENCE CHARACTERISTICS:
        (A) LENGTH: 176 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

Met Pro Glu Ala Ala Pro Pro Val Ala Pro Ala Ala Pro Thr
 1               5                  10                  15

Pro Ala Ala Pro Ala Pro Ala Pro Ser Trp Pro Leu Ser Ser Val
             20                  25                  30

Pro Ser Gln Lys Thr Tyr Gln Gly Ser Tyr Gly Phe Arg Leu Gly Phe
         35                  40                  45

Leu His Ser Gly Thr Ala Lys Ser Val Thr Cys Thr Tyr Ser Pro Ala
```

-continued

```
           50                  55                  60
Leu Asn Lys Met Phe Cys Gln Leu Ala Lys Thr Cys Pro Val Gln Leu
 65                  70                  75                  80

Trp Val Asp Ser Thr Pro Pro Gly Thr Arg Val Arg Ala Met Ala
                 85                  90                  95

Ile Tyr Lys Gln Ser Gln His Met Thr Glu Val Val Arg Arg Cys Pro
                    100                 105                 110

His His Glu Arg Cys Ser Asp Ser Asp Gly Leu Ala Pro Pro Gln His
                    115                 120                 125

Leu Ile Arg Val Glu Gly Asn Leu Arg Val Glu Tyr Leu Asp Asp Arg
    130                 135                 140

Asn Thr Phe Arg His Ser Val Val Pro Tyr Glu Pro Pro Glu Val
145                 150                 155                 160

Gly Ser Asp Cys Thr Thr Ile His Tyr Asn Tyr Met Cys Asn Ser Ser
                    165                 170                 175
```

(2) INFORMATION FOR SEQ ID NO:15:

(i) SEQUENCE CHARACTERISTICS:
        (A) LENGTH: 328 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:15:

```
Met Pro Glu Ala Ala Pro Pro Val Ala Pro Ala Ala Pro Thr
 1                   5                  10                  15

Pro Ala Ala Pro Ala Pro Ala Pro Ser Trp Pro Leu Ser Ser Ser Val
                    20                  25                  30

Pro Ser Gln Lys Thr Tyr Gln Gly Ser Tyr Gly Phe Arg Leu Gly Phe
                35                  40                  45

Leu His Ser Gly Thr Ala Lys Ser Val Thr Cys Thr Tyr Ser Pro Ala
    50                  55                  60

Leu Asn Lys Met Phe Cys Gln Leu Ala Lys Thr Cys Pro Val Gln Leu
 65                  70                  75                  80

Trp Val Asp Ser Thr Pro Pro Gly Thr Arg Val Arg Ala Met Ala
                 85                  90                  95

Ile Tyr Lys Gln Ser Gln His Met Thr Glu Val Val Arg Arg Cys Pro
                    100                 105                 110

His His Glu Arg Cys Ser Asp Ser Asp Gly Leu Ala Pro Pro Gln His
                    115                 120                 125

Leu Ile Arg Val Glu Gly Asn Leu Arg Val Glu Tyr Leu Asp Asp Arg
    130                 135                 140

Asn Thr Phe Arg His Ser Val Val Pro Tyr Glu Pro Pro Glu Val
145                 150                 155                 160

Gly Ser Asp Cys Thr Thr Ile His Tyr Asn Tyr Met Cys Asn Ser Ser
                    165                 170                 175

Cys Met Gly Gly Met Asn Arg Arg Pro Ile Leu Thr Ile Ile Thr Leu
                180                 185                 190

Glu Asp Ser Ser Gly Asn Leu Leu Gly Arg Asn Ser Phe Glu Val Arg
                195                 200                 205

Val Cys Ala Cys Pro Gly Arg Asp Arg Arg Thr Glu Glu Glu Asn Leu
    210                 215                 220

Arg Lys Lys Gly Glu Pro His His Glu Leu Pro Pro Gly Ser Thr Lys
```

```
                      225                 230                 235                 240
Arg Ala Leu Pro Asn Asn Thr Ser Ser Pro Gln Pro Lys Lys Lys
                    245                 250                 255

Pro Leu Asp Gly Glu Tyr Phe Thr Leu Gln Ile Arg Gly Arg Glu Arg
                260                 265                 270

Phe Glu Met Phe Arg Glu Leu Asn Glu Ala Leu Glu Leu Lys Asp Ala
            275                 280                 285

Gln Ala Gly Lys Glu Pro Gly Gly Ser Arg Ala His Ser Ser His Leu
        290                 295                 300

Lys Ser Lys Lys Gly Gln Ser Thr Ser Arg His Lys Lys Leu Met Phe
305                 310                 315                 320

Lys Thr Glu Gly Pro Asp Ser Asp
                325

(2) INFORMATION FOR SEQ ID NO:16:

(i) SEQUENCE CHARACTERISTICS:
        (A) LENGTH: 113 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

Met Cys Asn Ser Ser Cys Met Gly Gly Met Asn Arg Arg Pro Ile Leu
1               5                   10                  15

Thr Ile Ile Thr Leu Glu Asp Ser Ser Gly Asn Leu Leu Gly Arg Asn
                20                  25                  30

Ser Phe Glu Val Arg Val Cys Ala Cys Pro Gly Arg Asp Arg Arg Thr
            35                  40                  45

Glu Glu Glu Asn Leu Arg Lys Lys Gly Glu Pro His His Glu Leu Pro
        50                  55                  60

Pro Gly Ser Thr Lys Arg Ala Leu Pro Asn Asn Thr Ser Ser Ser Pro
65                  70                  75                  80

Gln Pro Lys Lys Lys Pro Leu Asp Gly Glu Tyr Phe Thr Leu Gln Ile
                85                  90                  95

Arg Gly Arg Glu Arg Phe Glu Met Phe Arg Glu Leu Asn Glu Ala Leu
            100                 105                 110

Glu (2) INFORMATION FOR SEQ ID NO:17:

(i) SEQUENCE CHARACTERISTICS:
        (A) LENGTH: 157 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:17:

Met Cys Asn Ser Ser Cys Met Gly Gly Met Asn Arg Arg Pro Ile Leu
1               5                   10                  15

Thr Ile Ile Thr Leu Glu Asp Ser Ser Gly Asn Leu Leu Gly Arg Asn
                20                  25                  30

Ser Phe Glu Val Arg Val Cys Ala Cys Pro Gly Arg Asp Arg Arg Thr
            35                  40                  45

Glu Glu Glu Asn Leu Arg Lys Lys Gly Glu Pro His His Glu Leu Pro
```

```
            50                  55                  60
Pro Gly Ser Thr Lys Arg Ala Leu Pro Asn Asn Thr Ser Ser Ser Pro
 65                  70                  75                  80

Gln Pro Lys Lys Lys Pro Leu Asp Gly Glu Tyr Phe Thr Leu Gln Ile
                 85                  90                  95

Arg Gly Arg Glu Arg Phe Glu Met Phe Arg Glu Leu Asn Glu Ala Leu
            100                 105                 110

Glu Leu Lys Asp Ala Gln Ala Gly Lys Glu Pro Gly Gly Ser Arg Ala
        115                 120                 125

His Ser Ser His Leu Lys Ser Lys Lys Gly Gln Ser Thr Ser Arg His
    130                 135                 140

Lys Lys Leu Met Phe Lys Thr Glu Gly Pro Asp Ser Asp
145                 150                 155
```

(2) INFORMATION FOR SEQ ID NO:18:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

```
Ser Val Glu Pro Pro Leu Ser Gln Glu Thr Phe Ser Asp Leu Trp Lys
 1               5                  10                  15

Leu Leu Pro Glu Asn Asn Val Leu Ser
            20                  25
```

(2) INFORMATION FOR SEQ ID NO:19:

(i) SEQUENCE CHARACTERISTICS:
        (A) LENGTH: 16 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:19:

```
Ser Gln Ala Met Asp Asp Leu Met Leu Ser Pro Asp Asp Ile Glu Gln
 1               5                  10                  15
```

(2) INFORMATION FOR SEQ ID NO:20:

(i) SEQUENCE CHARACTERISTICS:
        (A) LENGTH: 19 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

```
His Leu Lys Ser Lys Lys Gly Gln Ser Thr Ser Arg Met Lys Lys Leu
 1               5                  10                  15

Met Phe Lys
```

(2) INFORMATION FOR SEQ ID NO:21:

(i) SEQUENCE CHARACTERISTICS:
        (A) LENGTH: 723 base pairs
        (B) TYPE: nucleic acid (C) STRANDEDNESS: double
                (D) TOPOLOGY: linear (ii) MOLECULE TYPE: cDNA (iii) HYPOTHETICAL: NO (xi) SEQUENCE DESCRIPTION: SEQ ID NO:21:

| | | | | | |
|---|---|---|---|---|---|
| ATGGAGGAGC | CGCAGTCAGA | TCCTAGCGTC | GAGCCCCCTC | TGAGTCAGGA | AACATTTTCA | 60 |
| GACCTATGGA | AACTACTTCC | TGAAAACAAC | GTTCTGTCCC | CCTTGCCGTC | CCAAGCAATG | 120 |
| GATGATTTGA | TGCTGTCCCC | GGACGATATT | GAACAATGGT | TCACTGAAGA | CCCAGGTCCA | 180 |
| GATGAAGCTC | CCAGAATGCC | AGAGGCTGCT | CCCCCCGTGG | CCCCTGCACC | AGCAGCTCCT | 240 |
| ACACCGGCGG | CCCCTGCACC | AGCCCCCTCC | TGGCCCCTGT | CATCTTCTGT | CCCTTCCCAG | 300 |
| AAAACCTACC | AGGGCAGCTA | CGGTTTCCGT | CTGGGCTTCT | TGCATTCTGG | GACAGCCAAG | 360 |
| TCTGTGACTT | GCACGTACTC | CCCTGCCCTC | AACAAGATGT | TTTGCCAACT | GGCCAAGACC | 420 |
| TGCCCTGTGC | AGCTGTGGGT | TGATTCCACA | CCCCCGCCCG | GCACCCGCGT | CCGCGCCATG | 480 |
| GCCATCTACA | AGCAGTCACA | GCACATGACG | GAGGTTGTGA | GGCGCTGCCC | CCACCATGAG | 540 |
| CGCTGCTCAG | ATAGCGATGG | TCTGGCCCCT | CCTCAGCATC | TTATCCGAGT | GGAAGGAAAT | 600 |
| TTGCGTGTGG | AGTATTTGGA | TGACAGAAAC | ACTTTTCGAC | ATAGTGTGGT | GGTGCCCTAT | 660 |
| GAGCCGCCTG | AGGTTGGCTC | TGACTGTACC | ACCATCCACT | ACAACTACAT | GTGTAACAGT | 720 |
| TCC | | | | | | 723 |

(2) INFORMATION FOR SEQ ID NO:22:

(i) SEQUENCE CHARACTERISTICS:
            (A) LENGTH: 930 base pairs
            (B) TYPE: nucleic acid
            (C) STRANDEDNESS: double
            (D) TOPOLOGY: linear (ii) MOLECULE TYPE: cDNA (iii) HYPOTHETICAL: NO (xi) SEQUENCE DESCRIPTION: SEQ ID NO:22:

| | | | | | |
|---|---|---|---|---|---|
| ATGGATGATT | TGATGCTGTC | CCCGGACGAT | ATTGAACAAT | GGTTCACTGA | AGACCCAGGT | 60 |
| CCAGATGAAG | CTCCCAGAAT | GCCAGAGGCT | GCTCCCCCCG | TGGCCCCTGC | ACCAGCAGCT | 120 |
| CCTACACCGG | CGGCCCCTGC | ACCAGCCCCC | TCCTGGCCCC | TGTCATCTTC | TGTCCCTTCC | 180 |
| CAGAAAACCT | ACCAGGGCAG | CTACGGTTTC | CGTCTGGGCT | TCTTGCATTC | TGGGACAGCC | 240 |
| AAGTCTGTGA | CTTGCACGTA | CTCCCCTGCC | CTCAACAAGA | TGTTTTGCCA | ACTGGCCAAG | 300 |
| ACCTGCCCTG | TGCAGCTGTG | GGTTGATTCC | ACACCCCCGC | CCGGCACCCG | CGTCCGCGCC | 360 |
| ATGGCCATCT | ACAAGCAGTC | ACAGCACATG | ACGGAGGTTG | TGAGGCGCTG | CCCCCACCAT | 420 |
| GAGCGCTGCT | CAGATAGCGA | TGGTCTGGCC | CCTCCTCAGC | ATCTTATCCG | AGTGGAAGGA | 480 |
| AATTTGCGTG | TGGAGTATTT | GGATGACAGA | AACACTTTTC | GACATAGTGT | GGTGGTGCCC | 540 |
| TATGAGCCGC | CTGAGGTTGG | CTCTGACTGT | ACCACCATCC | ACTACAACTA | CATGTGTAAC | 600 |
| AGTTCCTGCA | TGGGCGGCAT | GAACCGGAGG | CCCATCCTCA | CCATCATCAC | ACTGGAAGAC | 660 |
| TCCAGTGGTA | ATCTACTGGG | ACGGAACAGC | TTTGAGGTGC | ATGTTTGTGC | CTGTCCTGGG | 720 |
| AGAGACCGGC | GCACAGAGGA | AGAGAATCTC | CGCAAGAAAG | GGGAGCCTCA | CCACGAGCTG | 780 |
| CCCCCAGGGA | GCACTAAGCG | AGCACTGCCC | AACAACACCA | GCTCCTCTCC | CCAGCCAAAG | 840 |
| AAGAAACCAC | TGGATGGAGA | ATATTTCACC | CTTCAGATCC | GTGGGCGTGA | GCGCTTCGAG | 900 |

ATGTTCCGAG AGCTGAATGA GGCCTTGGAA                                          930

(2) INFORMATION FOR SEQ ID NO:23:

(i) SEQUENCE CHARACTERISTICS:
        (A) LENGTH: 1062 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:23:

ATGGATGATT TGATGCTGTC CCCGGACGAT ATTGAACAAT GGTTCACTGA AGACCCAGGT           60

CCAGATGAAG CTCCCAGAAT GCCAGAGGCT GCTCCCCCCG TGGCCCCTGC ACCAGCAGCT          120

CCTACACCGG CGGCCCCTGC ACCAGCCCCC TCCTGGCCCC TGTCATCTTC TGTCCCTTCC          180

CAGAAAACCT ACCAGGGCAG CTACGGTTTC CGTCTGGGCT TCTTGCATTC TGGGACAGCC          240

AAGTCTGTGA CTTGCACGTA CTCCCCTGCC CTCAACAAGA TGTTTTGCCA ACTGGCCAAG          300

ACCTGCCCTG TGCAGCTGTG GGTTGATTCC ACACCCCCGC CCGGCACCCG CGTCCGCGCC          360

ATGGCCATCT ACAAGCAGTC ACAGCACATG ACGGAGGTTG TGAGGCGCTG CCCCCACCAT          420

GAGCGCTGCT CAGATAGCGA TGGTCTGGCC CCTCCTCAGC ATCTTATCCG AGTGGAAGGA          480

AATTTGCGTG TGGAGTATTT GGATGACAGA AACACTTTTC GACATAGTGT GGTGGTGCCC          540

TATGAGCCGC CTGAGGTTGG CTCTGACTGT ACCACCATCC ACTACAACTA CATGTGTAAC          600

AGTTCCTGCA TGGGCGGCAT GAACCGGAGG CCCATCCTCA CCATCATCAC ACTGGAAGAC          660

TCCAGTGGTA ATCTACTGGG ACGGAACAGC TTTGAGGTGC ATGTTTGTGC CTGTCCTGGG          720

AGAGACCGGC GCACAGAGGA AGAGAATCTC CGCAAGAAAG GGGAGCCTCA CCACGAGCTG          780

CCCCCAGGGA GCACTAAGCG AGCACTGCCC AACAACACCA GCTCCTCTCC CCAGCCAAAG          840

AAGAAACCAC TGGATGGAGA ATATTTCACC CTTCAGATCC GTGGGCGTGA GCGCTTCGAG          900

ATGTTCCGAG AGCTGAATGA GGCCTTGGAA CTCAAGGATG CCCAGGCTGG GAAGGAGCCA          960

GGGGGGAGCA GGGCTCACTC CAGCCACCTG AAGTCCAAAA AGGGTCAGTC TACCTCCCGC         1020

CATAAAAAAC TCATGTTCAA GACAGAAGGG CCTGACTCAG AC                           1062

(2) INFORMATION FOR SEQ ID NO:24:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:24:

ATGCCAGAGG CTGCTCCCCC CGTGGCCCCT GCACCAGCAG CTCCTACACC GGCGGCCCCT           60

GCACCAGCCC CCTCCTGGCC CCTGTCATCT TCTGTCCCTT CCCAGAAAAC CTACCAGGGC          120

AGCTACGGTT TCCGTCTGGG CTTCTTGCAT TCTGGGACAG CCAAGTCTGT GACTTGCACG          180

TACTCCCCTG CCCTCAACAA GATGTTTTGC CAACTGGCCA AGACCTGCCC TGTGCAGCTG          240

TGGGTTGATT CCACACCCCC GCCCGGCACC CGCGTCCGCG CCATGGCCAT CTACAAGCAG          300

```
TCACAGCACA TGACGGAGGT TGTGAGGCGC TGCCCCCACC ATGAGCGCTG CTCAGATAGC      360

GATGGTCTGG CCCCTCCTCA GCATCTTATC CGAGTGGAAG GAAATTTGCG TGTGGAGTAT      420

TTGGATGACA GAAACACTTT TCGACATAGT GTGGTGGTGC CCTATGAGCC GCCTGAGGTT      480

GGCTCTGACT GTACCACCAT CCACTACAAC TACATGTGTA ACAGTTCC                   528

(2) INFORMATION FOR SEQ ID NO:25:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:25:

ATGCCAGAGG CTGCTCCCCC CGTGGCCCCT GCACCAGCAG CTCCTACACC GGCGGCCCCT       60

GCACCAGCCC CCTCCTGGCC CCTGTCATCT TCTGTCCCTT CCCAGAAAAC CTACCAGGGC      120

AGCTACGGTT CCGTCTGGG CTTCTTGCAT TCTGGGACAG CCAAGTCTGT GACTTGCACG       180

TACTCCCCTG CCCTCAACAA GATGTTTTGC CAACTGGCCA AGACCTGCCC TGTGCAGCTG      240

TGGGTTGATT CCACACCCCC GCCCGGCACC CGCGTCCGCG CCATGGCCAT CTACAAGCAG      300

TCACAGCACA TGACGGAGGT TGTGAGGCGC TGCCCCCACC ATGAGCGCTG CTCAGATAGC      360

GATGGTCTGG CCCCTCCTCA GCATCTTATC CGAGTGGAAG GAAATTTGCG TGTGGAGTAT      420

TTGGATGACA GAAACACTTT TCGACATAGT GTGGTGGTGC CCTATGAGCC GCCTGAGGTT      480

GGCTCTGACT GTACCACCAT CCACTACAAC TACATGTGTA ACAGTTCCTG CATGGGCGGC      540

ATGAACCGGA GGCCCATCCT CACCATCATC ACACTGGAAG ACTCCAGTGG TAATCTACTG      600

GGACGGAACA GCTTTGAGGT GCATGTTTGT GCCTGTCCTG GGAGAGACCG GCGCACAGAG      660

GAAGAGAATC TCCGCAAGAA AGGGGAGCCT CACCACGAGC TGCCCCCAGG GAGCACTAAG      720

CGAGCACTGC CCAACAACAC CAGCTCCTCT CCCCAGCCAA GAAGAAACC ACTGGATGGA       780

GAATATTTCA CCCTTCAGAT CCGTGGGCGT GAGCGCTTCG AGATGTTCCG AGAGCTGAAT      840

GAGGCCTTGG AACTCAAGGA TGCCCAGGCT GGGAAGGAGC CAGGGGGGAG CAGGGCTCAC      900

TCCAGCCACC TGAAGTCCAA AAAGGGTCAG TCTACCTCCC GCCATAAAAA ACTCATGTTC      960

AAGACAGAAG GGCCTGACTC AGAC                                            984

(2) INFORMATION FOR SEQ ID NO:26:

(i) SEQUENCE CHARACTERISTICS:
        (A) LENGTH: 339 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:26:

ATGTGTAACA GTTCCTGCAT GGGCGGCATG AACCGGAGGC CCATCCTCAC CATCATCACA       60

CTGGAAGACT CCAGTGGTAA TCTACTGGGA CGGAACAGCT TTGAGGTGCA TGTTTGTGCC      120

TGTCCTGGGA GAGACCGGCG CACAGAGGAA GAGAATCTCC GCAAGAAAGG GGAGCCTCAC      180

CACGAGCTGC CCCCAGGGAG CACTAAGCGA GCACTGCCCA ACAACACCAG CTCCTCTCCC      240
```

CAGCCAAAGA AGAAACCACT GGATGGAGAA TATTTCACCC TTCAGATCCG TGGGCGTGAG      300

CGCTTCGAGA TGTTCCGAGA GCTGAATGAG GCCTTGGAA                            339

(2) INFORMATION FOR SEQ ID NO:27:

(i) SEQUENCE CHARACTERISTICS:
        (A) LENGTH: 471 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:27:

ATGTGTAACA GTTCCTGCAT GGGCGGCATG AACCGGAGGC CCATCCTCAC CATCATCACA      60

CTGGAAGACT CCAGTGGTAA TCTACTGGGA CGGAACAGCT TTGAGGTGCA TGTTTGTGCC     120

TGTCCTGGGA GAGACCGGCG CACAGAGGAA GAGAATCTCC GCAAGAAAGG GGAGCCTCAC     180

CACGAGCTGC CCCCAGGGAG CACTAAGCGA GCACTGCCCA ACAACACCAG CTCCTCTCCC     240

CAGCCAAAGA AGAAACCACT GGATGGAGAA TATTTCACCC TTCAGATCCG TGGGCGTGAG     300

CGCTTCGAGA TGTTCCGAGA GCTGAATGAG GCCTTGGAAC TCAAGGATGC CCAGGCTGGG     360

AAGGAGCCAG GGGGGAGCAG GGCTCACTCC AGCCACCTGA AGTCCAAAAA GGGTCAGTCT     420

ACCTCCCGCC ATAAAAAACT CATGTTCAAG ACAGAAGGGC CTGACTCAGA C             471

(2) INFORMATION FOR SEQ ID NO:28:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:28:

TCCCAAGCAA TGGATGATTT GATGCTGTCC CCGGACGATA TTGAACAA                   48

(2) INFORMATION FOR SEQ ID NO:29:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO:29:

AGCGTCGAGC CCCCTCTGAG TCAGGAAACA TTTTCAGACC TATGGAAACT ACTTCCTGAA      60

AACAACGTTC TGTCC                                                      75

(2) INFORMATION FOR SEQ ID NO:30:

(i) SEQUENCE CHARACTERISTICS:
        (A) LENGTH: 57 base pairs
        (B) TYPE: nucleic acid
        (C) STRANDEDNESS: double -continued

```
      (D) TOPOLOGY: linear (ii) MOLECULE TYPE: cDNA (iii) HYPOTHETICAL: NO (xi) SEQUENCE DESCRIPTION: SEQ ID NO:30:

CACCTGAAGT CCAAAAAGGG TCAGTCTACC TCCCGCCATA AAAAACTCAT GTTCAAG        57
```

METHOD OF DETECTING P53-SPECIFIC ANTIBODIES

The invention relates to a method of detecting p53-specific antibodies in body fluids. It further relates to a kit useful therefor. Also, the invention relates to p53 fragments and DNA sequences coding for them, said fragments comprising binding regions for p53-specific antibodies, as well as to methods of preparing them.

Eukaryotic cells are known to express a protein identified as p53 (p53). This protein is known in terms of its primary structure and comprises 393 amino acids (see Lamb, P. and Crawford, L. V., Mol. Cell. Biol., Vol. 6 (1986), 1379–1386). Increased expression of p53 is found in many tumor diseases. This may be accompanied by the presence of specific anti-p53 antibodies. A variety of methods for the detection of such antibodies have been reported. For instance, p53-containing cell extracts are radioactively labelled in vivo and immunoprecipitated with sara from patients (see de Fromentel, C.C. et al., Int. J. Cancer 39 (1987), 185–189). Also, anti-p53 antibodies are coated on supports where p53 is adsorbed from cell extracts and added to sera from patients. Bound anti-p53 antibodies are detected with iodine-coupled protein A (see Crawford, L. V. et al., Mol. Biol. Med. 2 (1984), 261–272).

In those methods of detection radioactive substances are employed. This means higher safety risk and thus limited utility, especially in hospitals. Further, as the in vivo labelling of cells is expensive and requires extensive equipment, this method is useful only to a limited extent in large-scale, serial experiments. Also, the use of cell extracts frequently leads to unspecific antibody binding.

Therefore, it is the object of the present invention to provide a method of detecting p53-specific antibodies that does not involve the aforementioned drawbacks.

In accordance with the invention, this object is achieved by a method in which support-bound p53 and/or support-bound fragments thereof comprising binding regions for p53-specific antibodies are incubated with body fluids and the specific antibodies (a) bound to p53 and/or fragments thereof are allowed to react with labelled antibodies (b) directed against antibodies (a), or with unlabelled antibodies (b) while the latter are allowed to react with labelled antibodies (c) directed against antibodies (b), with the labelling being non-radioactive in either case.

The term "p53" includes a p53 protein comprising a wild-type sequence. Such a protein can be isolated from cells such as HepG2 (see Knowles, B. et al., Science 209 (1990), 497–499). p53 may also have a sequence other than one of the wild type. Such a sequence may include additions, deletions and/or substitutions of one or more amino acids. Further, p53 may be part of a fusion protein. Such a protein, like any other p53, can be isolated from cells expressing said protein after genetic engineering. Such cells include both prokaryotic and eukaryotic cells. Examples of the former include E. coli strains such as BL21 (see Studier, F. W. et al., Methods in Enzymology 185 (1990), 60–89), while the latter are exemplified especially by mammal, yeast and insect cells. Genetic engineering includes conventional methods known in the art whereby nucleic acids having particular sequences are prepared, inserted in cells and expressed. Anybody skilled in the art is aware of the materials such as vectors and conditions useful in those methods (see, egg., Maniatis, T. et al., Cold Spring Harbor Laboratory, 1982).

According to the invention, a p53 cDNA from HepG2 cells (see above) is subjected to reverse transcriptase in a conventional manner and amplified in a common PCR process. The cDNA is compared to published data (egg., EMBL gene library) in terms of its sequence and inserted in the known vector pet 3d to give the recombinant vector pet 92/2. This vector is transformed to the bacterial strain BL21 (see above) to express p53. p53 induction is achieved by adding IPTG. The bacteria are sedimented and subjected to lysozyme and DNase I treatment after freezing and thawing. The lysates are incubated with urea solutions having different concentrations, and p53 is released after centrifugation and obtained in pure form by polyacrylamide gel electrophoresis followed by electroelution. Anybody skilled in the art is aware of the above methods as well as the materials and conditions necessary therefor.

In accordance with the invention, there are provided p53 fragments containing binding regions for p53-specific antibodies. Such fragments will hereinafter be referred to as p53 ABBR fragments. Preferably, the p53 ABBER fragments comprise amino acids 1–241, 40–349, 40–393, 66–241, 66–393, 237–349, and 237–393 as well as 9–33, 37–52, and 368–386 of p53 (corresponding to SEQ ID NOS 11–20).

Several methods can be used to produce p53 ABBR fragments. Of them, one method has turned out to be quite favorable. It comprises constructing fragments at locations spread all over the entire length of p53, with at least two fragments each comprising an overlapping region, allowing said fragments to react with a p53-specific antibody, identifying the overlapping region bound by the antibody to provide the p53 ABBR fragment, as well as optionally using said fragment as a basis to repeat the above cycle one or more times.

This method starts out by using a p53 CDNA obtained from HepG2 cells (see above). Based thereon, DNA fragments at locations spread over the entire length of the cDNA are amplified in a common PCR process, with at least two fragments each comprising an overlapping region. The amplified DNA fragments are inserted in pet 3d and expressed in the bacterial strain BL21 after transformation and IPTG induction, as described above. The resulting p53 fragments are isolated and subjected to polyacrylamide gel electrophoresis, as described above for p53. This is followed by Western blot analysis using labelled, commonly available p53-specific antibodies, e.g., Pab 240 for binding to the p53 fragments. The binding region of the antibody is assigned to the overlapping region by binding one of said antibodies to two p53 fragments comprising an overlapping region. This region provides the fragment identified as p53 ABBR. To do this, a common PCR process is used, for example. In using the p53 ABBR fragment, the above cycle can be repeated one or more times to further limit the binding region of the p53-specific antibody. Said binding region can be limited to a few amino acids. Short p53 fragments that might be necessary for this can be prepared synthetically. Anybody skilled in the art is aware of the above methods as well as the materials and conditions necessary to carry them out.

In accordance with the invention, there are also provided the DNA sequences coding for p53 ABBR fragments. Preferably, such DNA sequences comprise the nucleotides coding for amino acids 1–241, 40–349, 40–393, 66–241, 66–393, 237–349, and 237–393 as well as 9–33, 37–52, and 368–386 of p53 (corresponding to SEQ ID NOS 21–30).

In accordance with the invention, p53 and/or p53 ABBR fragments are bound to support material. of course, it is also possible to bind thereto a p53 ABBR fragment individually or in combination with p53. The support material includes any material useful in binding proteins, especially microtiter plates, tubes, micropellets, or slides. In the case of very small p53 ABBR fragments, especially peptides, it is advisable to bind the protein to the support material via conventional carriers, e.g., BSA. Such binding as well as one without any support can be achieved by using conventional methods. According to the invention, microtiter plates are used as supports. p53 and/or p53 ABBR fragments are incorporated in carbonate buffers, diluted to different concentrations and poured into the wells of microtiter plates. After incubation overnight at 4° C., several washings are performed in physiological buffer. The binding of p53 and/or p53 ABBR fragments is stable.

In accordance with the invention, bound p53 and/or bound p53 ABBR fragments are incubated with body fluids. Such body fluids include any fluids obtained from an animal body, particularly from mammals, and most particularly from a human body. The fluids preferably comprise serum, lymph, saliva and urine. They further include fluids that can be isolated from solid tissue, such as lungs, brain and bone marrow, as well as from tumors, such as colorectal carcinomas and hepatocell carcinomas. Incubation is performed by using conventional methods. According to the invention, sera from patients are diluted to different concentrations and added to the bound p53 and/or bound p53 ABBR fragments in the microtiter plate. After incubation for one hour at 37 c, several washings are performed in physiological buffer. The binding of specific anti-p53 antibodies is stable.

In accordance with the invention, such bound antibodies (hereinafter referred to as antibodies (a)) are reacted with labelled antibodies (b) directed against antibodies (a), or with unlabelled antibodies (b) while the latter is reacted with labelled antibodies (c) directed against antibodies (b).

In either case the labelling is non-radioactive. Rather, other conventional labels are used. Useful labels include especially fluorescent dyes such as, e.g., fluorescein isothiocyanate, and enzymes such as alkaline phosphatase or peroxidase. The amplifier system may be a biotin/streptavidine complex. The labels are commonly available. Conjugation with antibodies (b) or (c) is performed as prescribed by the manufacturer. Prelabelled antibodies (b) and (c) are also commonly available.

The choice of appropriate antibodies (b), either labelled or unlabelled, depends on what animal, or what type of animal, the used body fluid comes from. If, for example, the fluid comes from a human body, antibodies (b) will be those directed against human immunoglobulin. Analogously, if antibodies (c) are used in addition, these will be chosen in relation to the animal, or type of animal, antibodies (b) come from. The choice of appropriate antibodies is known to those skilled in the art and can be made readily.

Bound antibodies (a) can be reacted with labelled antibodies (b) or with unlabelled antibodies (b) and then with labelled antibodies (c) in a conventional manner. In accordance with the invention, their reaction with antibodies (b) in both alternatives proceeds within one hour at 37° C. After several washings, a substrate solution corresponding to the label is added in the first alternative to initiate the detection reaction. This is done as prescribed by the manufacturer. In the second alternative antibodies (c) are added after the washings.

Their reaction and the initiation of the detection reaction proceed analogously.

The method of the invention exhibits high sensitivity. Such sensitivity is particularly high where antibodies (c) are used in addition. Furthermore, the present method can be employed rapidly in any laboratory. It is not necessary to take any precautionary measures. The method of the invention is therefore particularly useful in conducting large-scale, serial experiments.

In accordance with the invention, there is also provided a kit useful in carrying out the above methods. Said kit contains support-bound p53 and/or support-bound p53 ABBR fragments and labelled antibodies (b) as well as conventional buffers for washing and a substrate corresponding to the label, or support-bound p53 and/or support-bound p53 ABBR fragments, unlabelled antibodies (b) and labelled antibodies (c) as well as conventional buffers for washing and a substrate corresponding to the label.

In either case the labelling is non-radioactive. The observations made above regarding the method of the invention equally apply to the labelling as well as to the other components of the kit.

SEQ ID NOs 16–22 show the amino acid sequences of preferred p53 ABBR fragments.

SEQ ID NOs 23–30 show the DNA sequences of the p53 ABBR fragments listed on SEQ ID NOs 16–22.

The present invention will be further illustrated by the following examples.

EXAMPLE 1

Expression of p53 and His-p53 fusion protein (A) Expression of D53

A p53 CDNA from the HepG2 cell line (see above) was subjected to reverse transcriptase using a hexamer random primer and amplified in a common PCR process using the "Fo" and "$R_{11}$" oligo primers ("Fo" sequence SEQ ID NO: 1: GCA TGG ATC CGA ATT CTG CCT TCC GGG TCA CTG C; "$R_{11}$" SEQ ID NO: 2: GGT ACC CGG GGA TCC TGG GTG CTT CTG ACG). The amplified sequence was compared to published data (EMBL gene library) and cloned into vector pet3d in the bacterial strain HMS 174 via restriction enzyme sites at the initiation codon of p53 (NcoI) and in the $R_{11}$ primer (BamHI) to give the entire coding region. The resulting vector pet 92/2 was transformed into the bacterial strain BL21 (see above) to express p53. After cultivation of the bacteria at 37° C. to obtain an optical density of 0.6 (600 nm) in an LB medium containing 100 µg/ml ampicillin and 30 µg/ml chloroamphenicol, a three-hour induction of p53 at 30° C. was performed using 2mM IPTC.

(B) Expression of His-P53 fusion protein

A p53 cDNA from the HepG2 cell line (see above) was subjected to reverse transcriptase and amplified by PCR using the "Fp53-B" and "His-Rp53" oligo primers ("Fp53" sequence: SEQ ID NO: 3 CGC GGA TCC ATG GAG GAG CCG CAG TCA G; "His-Rp53" SEQ ID NO: 4: CGC GGA TCC TCA ATG GTG ATG GTG ATG GTG GTC TGA GTC AGG CCC TTC TG). The amplified sequence was cloned into the known expression vector pQE-8, that had been opened using BamHI. Said p53 protein, which is linked to six histidines at either end, is expressed in the bacterial strain *E. coli* SG13009 (see Gottesmann, S. et al., J. Bacteriol. 148 (1981), 265–273). After cultivation of the bacteria at 37° C. to obtain an optical density of 0.6 in an LB medium containing 100 µg/ml ampicillin and 25 µg/ml canamycin, a six-hour induction of His-p53 fusion protein at 37° C. was performed using 1 mM IPTG.

EXAMPLE 2

Isolation and purification of p53 and His-p53 fusion protein (A) Isolation and purification of P53

After p53 induction, 400 ml of bacterial culture of Example 1 (A) were sedimented by centrifugation for 10 minutes at 500 g, rinsed in 50 mM Tris-HCl, pH 8.0, 100 mM NaCl and again centrifuged. After freezing and thawing, the sediment was resuspended in 1.6 ml of lysis buffer (50 mM Tris-HCl, pH 8.0, 10% sucrose). To this lysozyme (final conc. 2 mg/ml) and 0.5 M EDTA (final conc. 50 EM) were successively added. After 20-minute incubation on ice, $MgCl_2$ (final conc. 80 mM) and DNAse I (250 µg) was added, followed by incubation for 10 minutes at room temperature (final volume 6.5 ml). To this 10 µl of 0.1 M PMSF were added, and the mixture was centrifuged for 15 minutes at 10,000 g and 4° C. This centrifugation step was repeated three times, each after resuspending the sediment and 10-minute incubation in 1 M, 3 M and 7 M urea, respectively, with PMSF (0.1 M, 10 µl). The supernatant of the last centrifugation step was further purified as follows: After gel electrophoresis in a 10% polyacrylamide gel, excision of the desired protein band and overnight electro-elution at 4° C. in 25 mM Tris-HCl, 0.2 M glycine, 0.5% SDS, pH 8.8, in a commonly available biotrap elution chamber, p53 was obtained in pure form.

(B) Isolation and 12purification of His-p53 fusion protein 250 ml of bacterial culture of Example 1 (B) were sedimented after induction of the His-p53 fusion protein and washed once in 40 ml of PBS. 1 g of bacterial pellet each was subjected to sonification in 3 ml of solution A for 1 min. and then stirred on a mnagnetic stirrer at medium speed and RT for 8–12 hrs. The resulting suspension was again sedimented at 15,000 rpm and RT for 30 mins. 2–6 ml of the resulting supernatant were placed on a conventional nickel chelate chromatography column (Ni-NTA resin). The column material had been pre-washed with 3 column volumes of solution A (see above). Upon charging the bacterial extract, the column was washed successively with solutions A to F, viz. with 2–3 column volumes of the respective solution, until no protein could be eluted any more. The protein content of the collected fractions was determined photometrically by extinction measurement at 280 nm, with 1 OD corresponding to about 1 mg of protein/ml. The His-p53 fusion protein was contained in the fractions after elution with solution D or E, usually showing only a very small content of bacterial protein. To remove this content, the eluted protein could again be bound to the Ni NTA resin column by adjusting the pH of the combined fragments with the main portion of the protein to be purified to pH 8.0 and by placing these again on the column. The subsequent elution was performed with solutions A to F, as described above. The purity and quality of the eluted His-p53 fusion protein was examined by SDS PAGE.

Ingredients of the solutions used:

Solution A: 6 M guanidinium hydrochloride, 0.1 M $NaH_2PO_4$, 10 mM β-mercaptoethanol, 0.01 M TrisHCl, pH 8.0

Solution B: 8 M urea, 0.1 M $NaH_2PO_4$, 0.01 M TrigHCl, pH 8.0

Solution C: 8 M urea, 0.1 M $NaH_2PO_4$, 0.01 M TrisHCl, pH 6.3

Solution D: 8 M urea, 0.1 M $NaH_2PO_4$, 0.01 M TrisHCl, pH 5.9

Solution E: 8 M urea, 0.1 M $NaH_2PO_4$, 0.01 M TrisHCl, pH 4.5

Solution F: 6 M guanidinium hydrochloride, 0.2 M acetic acid

The above method in (B) is characterized by an extremely rapid and efficient purification of the expressed protein.

EXAMPLE 3

Preparation of p53-ABBR and His-p53 ABBR fragments (A) preparation of a p53-ABBER-fragment Two overlapping DNA sequences from the CDNA obtained from the Hep G2 cell line (see above) were amplified in a common PCR process using the oligo primer pairs "Fp 53-B"/"Rp 53–55" and "Fp 53–30"/"Rp 53–70". One DNA sequence coded for a p53 fragment of amino acids 1–55 while the other coded for a p53 fragment of amino acids 30–70. The sequences of the oligo primers used were the following:

"Fp 53-B" SEQ ID NO: 5
CGCGGATCCATGGAGGAGCCGCAGTCAG, "Rp 53–55" SEQ ID NO: 6
CGCGGATCCTCAAGTGAACCATTGTTCAATATCGTC CG, "Fp 53–30" SEQ ID NO: 7
CGCGGATCCAACGTTCTGTCCCCCTTGCCG, "Rp 53–70" SEQ ID NO: 8
CGCGGATCCTCAAGCAGCCTCTGGCATTCTGGG SEQ ID NO: 9.

The amplified sequences were compared to published data (EMBL gene library) and cloned into the vector pet 3 d (see above) via the restriction enzyme site BamHI. The sequences were expressed in the bacterial strain BL21 (see above) after transformation and IPTG induction. The expressed sequences (p53 fragments) were isolated and subjected to polyacrylamide gel electrophoresis, as described in Example 2 (A) for p53. This was followed by conventional Western blot analysis using a commonly available p53-specific antibody for binding to the p53 fragments. Said antibody bound to both overlapping p53 fragments. The overlapping region, i.e., amino acids 30–55 was considered to be the binding region of the antibody Said binding region was further limited in the manner shown above by using two synthetic, overlapping p53 peptides. Thus, it was possible to limit the binding region of the p53-specific antibody to the p53 ABBR fragment of amino acids 37–52.

(B) Preparation of a His-p53 ABBR fragment

Two overlapping DNA sequences from the cDNA obtained from the Hep G2 cell line (see above) were amplified in a common PCR process using the oligo primer pairs "Pp 53–B"/"Rp 53–55-His" and "Fp 53–30"/"Rp 53–70-His". One DNA sequence coded for a p53 fragment of amino acids 1–55 while the other coded for a p53 fragment of amino acids 30–70 (see (A) above). The sequences of the oligo primers used were the following: "Fp 53-B" (see (A) above), "Rp 53–55-His" SEQ ID NO: 9
CGCGGATCCTCAATGGTGATGGTGATGGTGAGTGA ACCATTGTTCAATATCGTCCG, "Fp 53–30"(see (A) above), "Rp 53–70-His SEQ ID NO: 10
CGCGGATCCTCAATGGTGATGGTGATG-GTGAGCAGCCTCTGGCATTCTGGG.

The amplified sequences were compared to published data (EMBL gene library) and cloned into the vector pQE-8 (see above) via the restriction enzyme site BamHI. The sequences were expressed in the bacterial strain E. coli SG 13009 (see above) after transformation and IPTG induction. The expressed sequences (His-p53 fragments) were isolated and subjected to polyacrylamide gel electrophoresis, as described in Example 2 (B) for His-p53. This was followed by conventional Western blot analysis using a commonly available p53-specific antibody for binding to the His-p53 fragments. Said antibody bound to both overlapping p53 fragments. As described in (A) above, the overlapping region, i.e., amino acids 30–55 was considered to be the binding region of the antibody. As described in (A) above, said binding region was further limited to amino acids 37–52 in the manner shown above.

EXAMPLE 4

Detection by p53 of specific p53 antibodies in the serum from patients

To perform an ELISA, p53 of Example 2 (A) was incorporated in 0.1 M carbonate buffer (sodium carbonate/sodium hydrogen carbonate, pH 9.6). To coat a 96-well microtiter plate, 100 μl of carbonate buffer were each applied in rows with 0.2 ng, 0.15 ng, 0.1 ng, 0.05 ng, 0.01 ng and 0.005 ng of p53 and using 1% BSA solution as the control. After incubation overnight at 4° C., ten short washings were performed using PBS. A serum from a patient suffering from a hepatocellular carcinoma diluted at 1:100, 1:250, 1:500 and 1:1000 (dilution in 500 mg of BGG/l, 100 mg of BSA/l, 0.05% Tween-20) was added to each of the different p53 concentrations and the BSA control and incubated for one hour at 37° C. ("chessboard titration"). This was followed by five washings with PBS containing 0.05% Tween-20. A commonly available peroxidase-coupled goat anti-human antibody was diluted as prescribed by the manufacturer (100 mg/l of BGG, 500 mg/l of BSA, 0.05% Tween-20). This was followed by three washings with PBS. The peroxidase detection reaction was performed with OPD initiation solution. To do this, a 0.1 M $Na_2HPO_4$ solution with 0.1 M $KH_2PO_4$ was adjusted to pH 6.0. To 20 ml of this buffer 30 mg of O-phenylene diamine dihydrochloride (OPD) were dissolved and 35 μl of 35% $H_2O_2$ were added shortly before application. 150 μl of initiation solution were added per well. After five-minute incubation the reaction was terminated with 75 μl 4 M $H_2SO_4$ and the color intensity was determined photometrically at 492 nm. Absorption values more than twice the BSA control were considered to be a positive reaction.

Table 1 shows the data of a thus performed ELISA compared to the determination of specific antibodies by the immunoblot technique. The fact that the two methods were almost identical demonstrates that the anti-p53 ELISA is suitable for serial testing of clinical material. Further, the ELISA shows greater sensitivity than the immunoblot technique, thus emphasizing the suitability of the ELISA as the primary testing procedure.

TABLE 1

Detection of specific p53-antibodies in sera from patients suffering from a hepatocellular carcinoma by immunoblot and ELISA techniques using p53

| Serum code: | 5  | 9 | 10 | 11 | 13 | 14 | 15 | 18 | 28 | 29 | 38 |
|---|---|---|---|---|---|---|---|---|---|---|---|
| Immunoblot: | −  | + | −  | −  | −  | −  | +  | +  | −  | +  | +  |
| ELISA:      | +− | + | +− | −  | +− | +  | −  | +  | −  | +  | +  |

Legend:
Immunoblot:
+: a visible band at the level of a protein having a molecular weight of 53 kD at a serum dilution of 1:15, incubation with alkaline phosphatase-coupled, human-specific goat antibody (1:5000) and alkaline phosphatase detection reaction.
−: no visible signal
ELISA:
−: absorption value below twice the BSA control value
+−: absorption value around twice the BSA control value
+: absorption value at least twice the BSA control value in all dilutions

---

We claim:

1. A method of detecting p53-specific antibodies in body fluids comprising:
   I incubating a sample of body fluids suspected of containing p53-specific antibodies with support-bound p53 fragments consisting of binding regions for p53 specific antibodies and then either
   II(a) reacting the incubated sample from Step I with labeled antibodies directed against the p53-specific antibodies, or
   II(b) reacting the incubated sample from Step I with unlabeled antibodies directed against the p53-specific antibodies followed by reacting with labeled antibodies directed against the unlabeled antibodies,
   wherein the labeled antibodies are non-radioactive;
   wherein the binding of labeled antibodies indicates the presence of p53-specific antibodies and
   wherein said p53 fragments are selected from the group consisting of amino acids 237–349 (SEQ ID NO: 16), 237–393 (SEQ ID NO: 17), 9–33 (SEQ ID NO: 18), 37–52 (SEQ ID NO: 19), and 368–386 (SEQ ID NO: 20) of p53.

2. The method as defined in claim 1 wherein the body fluids are selected from the group consisting of serum, lymph, saliva, urine and fluids obtained from solid tissue and tumors.

3. The method as defined in claim 1 wherein the p53 fragments are obtained by expression of a cDNA sequence.

4. The method as defined in claim 1 wherein the support of the support-bound p53 fragments is selected from the group consisting of microtiter plates, tubes, micropellets, and slides.

5. The method as defined in claim 1 wherein said labeled antibodies are labelled with an enzyme.

6. The method as defined in claim 1 wherein said labeled antibodies are labelled with a fluorescent dye.

7. A kit containing:
   I.A). support-bound p53 fragments consisting of binding regions for p53-specific antibodies wherein said fragments are selected from the group consisting of amino acids 237–349 (SEQ ID NO: 16), 237–393 (SEQ ID NO: 17), 9–33 (SEQ ID NO: 18), 37–52 (SEQ ID NO: 19), and 368–386 (SEQ ID NO: 20) of p53,
   I.B). either labeled antibodies directed against said p53-specific antibodies or unlabeled antibodies directed against said p53-specific antibodies plus labeled antibodies directed against said unlabeled antibodies,
   I.C). conventional buffers for washing and
   I.D). optionally a substrate with which said labeled antibodies react.

8. A p53 fragment consisting of a binding region for p53-specific antibodies wherein said fragment is selected from the group consisting of amino acids 237–349 (SEQ ID NO:16), 237–393 (SEQ ID NO:17), 9–33 (SEQ ID NO:18), 37–52 (SEQ ID NO:19) and 368–386 (SEQ ID NO:20) of p53.

9. An isolated nucleic acid consisting of a DNA encoding a p53 fragment as defined in claim 8.

* * * * *